United States Patent [19]

Marks

[11] Patent Number: 5,746,213
[45] Date of Patent: May 5, 1998

[54] ADJUSTABLE BLOOD PRESSURE CUFF AND METHOD OF USING SAME

[76] Inventor: Lloyd A. Marks, 727 Great Springs Rd., Bryn Mawr, Pa. 19010

[21] Appl. No.: 394,304

[22] Filed: Feb. 24, 1995

[51] Int. Cl.$^6$ ............................................. A61B 5/02
[52] U.S. Cl. ................................................. 128/686
[58] Field of Search ..................... 128/686; 606/201–4

[56] References Cited

U.S. PATENT DOCUMENTS

| | | |
|---|---|---|
| 3,467,077 | 9/1969 | Cohen . |
| 3,765,405 | 10/1973 | Natkanski . |
| 3,773,036 | 11/1973 | Weyer ........................... 128/686 |
| 4,745,924 | 5/1988 | Ruff . |
| 5,243,991 | 9/1993 | Marks . |
| 5,396,894 | 3/1995 | Eide et al. ..................... 128/686 |
| 5,511,552 | 4/1996 | Johnson ......................... 128/686 |
| 5,513,643 | 5/1996 | Suite ............................. 128/686 |

*Primary Examiner*—John P. Lacyk
*Attorney, Agent, or Firm*—Wigman, Cohen, Leitner & Myers, P.C.

[57] ABSTRACT

An adjustable and disposable blood pressure cuff comprises a bladder provided with adhesive layers on both sides thereof which are covered by peelable strips. According to the method of using the cuff, selected strips or portions thereof on one side of the cuff are peeled away and removed. The cuff is then folded and adhesively secured to itself at the optimum width for the circumference of the limb of the patient. Selected strips or portions thereof on the other side of the cuff are peeled away and removed so that the cuff may be adhesively secured about the limb of a patient. In a second embodiment, a hook-and-loop fastener piece replaces the adhesive layer on the other side of the cuff for securing the cuff about the limb of a patient.

29 Claims, 3 Drawing Sheets

ADJUSTABLE BLOOD PRESSURE CUFF AND METHOD OF USING SAME

FIELD OF THE INVENTION

The present invention relates to a method of and an apparatus for measuring blood pressure and more particularly to an improved adjustable blood pressure cuff and a method of using the cuff to measure blood pressure in proportion to the circumference of the limb upon which the blood pressure is measured.

BACKGROUND OF THE INVENTION

In my prior U.S. Pat. No. 5,243,991, the disclosure of which is incorporated herein by reference, there is disclosed an adjustable blood pressure cuff and a method of measuring blood pressure. My prior cuff and method avoid the errors resulting from using a blood pressure cuff having an improper width in relation to the circumference of the limb of the patient whose blood pressure is to be measured. That is accomplished by providing a flexible bladder which is foldable upon and removably retained to itself by means of hook-and-loop fasteners, such as Velcro® fasteners, attached to both sides of the bladder. In this way, a cuff width, such as 0.4 times the circumference of the limb as recommended by the American Heart Association, can be set by folding over and removably securing the hook-and-loop fasteners to achieve the appropriate cuff width. An additional feature of my prior invention is the provision of an index line on the cuff having a cuff width to limb circumference ratio of 0.4:1. Using this index line, the proper fold line can be easily determined for any given limb circumference. While my prior invention solves a long-felt need in the art for a blood pressure cuff which is easily adjustable for use on a variety of patients, regardless of the size of the limbs of the patient, it would be desirable to provide such a blood pressure cuff that may be adjusted for use with a particular patient and then disposed of after one or several uses on that patient and that minimizes the use of the relatively expensive hook-and-loop fasteners which also tend to collect lint.

In medical technology, the concept of disposability of medical devices used in patient care is well-known. The disposability of some medical devices, however, is limited by the initial cost of the devices so that it is simply impractical to make some medical devices disposable. It would be desirable therefore to produce a blood pressure cuff of relatively inexpensive and simple construction so that it may be disposed of after one or several uses.

SUMMARY OF THE INVENTION

In view of the foregoing, it should be apparent that there exists a need in the art for a disposable blood pressure cuff which is adjustable in width for use with a particular patient, and then after one or several uses may be discarded or otherwise disposed of. It is, therefore, a primary objective of the present invention to fulfill that need by providing a blood pressure cuff which is simple and inexpensively constructed and a method of quickly and conveniently adjusting the width and circumference of the cuff to the appropriate dimension for the limb of a particular patient.

Another object of the invention is to provide an improved, inexpensive blood pressure cuff which has substantially all the advantages and features of my aforementioned adjustable blood pressure cuff, but which may be discarded after one or several uses on a single patient.

It is another object of the present invention to provide an improved blood pressure cuff which can be readily adjusted to the proper width in relation to the circumference of a limb of a patient and then secured in a permanent annular configuration for reuse when necessary with the same patient.

It is a further object of the invention to eliminate or minimize the use of hook-and-loop fastener materials so as to make the blood pressure cuff of the invention less expensive and more flexible to folding.

Briefly described, the above objectives are accomplished according to the method and apparatus aspects of the present invention by providing a flexible, inflatable bladder having a width and length and first and second side surfaces on which adhesive layers are provided and covered with a plurality of selectively oriented, peelable strips. After selection and removal of one or more of the peelable strips from appropriate locations on one side surface of the bladder, a portion of the bladder may be folded along the length of the bladder and the adhesive layer pressed into contact with such side surface to adhesively secure the folded-over bladder portion to the other bladder portion. In this way, the width of the blood pressure cuff may be adjusted to the actual circumference of the limb of a particular patient so that accurate blood pressure measurements may be obtained for that patient. To the extent an accurate blood pressure measurement is made by invasive means, it is also possible to further adjust the width of the cuff to match the invasively-measured blood pressure.

After the width of the blood pressure cuff has been adjusted as described above, it is wrapped about the limb of the patient with the folded portion facing outwardly. Selected ones of the peelable strips on the folded portion and on the inwardly facing or second side surface of the bladder are peeled off to expose selected portions of the adhesive layer on the second side surface. This adhesive layer is pressed into contact with the opposing bladder/adhesive surfaces to secure the blood pressure cuff in an annular configuration about the limb of the patient. The cuff is preferably secured in a sufficiently loose condition so that it can be slid off and back onto the limb in its annular configuration, but not so loose that inflation of the bladder does not cause the bladder to engage the limb circumferentially with sufficient pressure to be operable. Those skilled in the art are aware of the known errors that may result from a blood pressure cuff that is positioned too loosely on the limb. Such errors should be avoided.

The peelable strips are made from sheet material which is cut, scored or perforated in appropriate locations so as to permit essentially universal adjustment and securement of the cuff in width and annular circumference for any limb circumference within the range of the cuff. It is contemplated and is within the scope of the invention to provide more than one size of adjustable blood pressure cuff, e.g., one size for infants, another size for children and adult patients and a third size for unusually large or obese patients.

In a second embodiment of the invention, instead of an adhesive layer on the second side surface of the bladder, a fastener piece comprising two rectangular sections of hook-and-loop fastener material fastened together is provided with adhesive layers on both sides of the fastener piece and each adhesive layer is covered with a peelable backing or peelable strips. After the cuff is folded, the peelable backing is removed from the adhesive layer on one of the two rectangular sections and the fastener piece is adhesively attached by such adhesive layer to the cuff in a central location adjacent one transverse edge of the cuff. The cuff is then wrapped about the patient's limb and one or more peelable strips are peeled away to expose the second adhesive layer to which the free end of the cuff is applied to secure the cuff in the above-described annular configuration about the limb of the patient.

Advantageously, in both embodiments, the bladder is provided with a tube or tubes in communication with the internal volume or inflation chamber of the bladder. The tubes may have adapters for removable attachment to a conventional inflation/deflation device and a suitable pressure gauge. As in my prior patent, an index line may be provided on one surface of the bladder for determining the ideal width of the blood pressure cuff for a particular limb circumference. The index line may be a straight line with the slope x=0.4 y as recommended by the American Heart Association, where x is the ideal width dimension of the cuff and y is the circumference of the limb of the patient at which blood pressure is to be measured. The index line may also be another line, e.g., a curved line that may have a better correlation between invasive and non-invasive blood pressure measurements.

With the foregoing and other objects and advantages and features of the invention that will become hereinafter apparent, the nature of the invention may be more clearly understood by reference to the following detailed description of the invention, the appended claims and to the several views illustrated in the attached drawings.

DETAILED DESCRIPTION OF THE INVENTION

Figure 1:
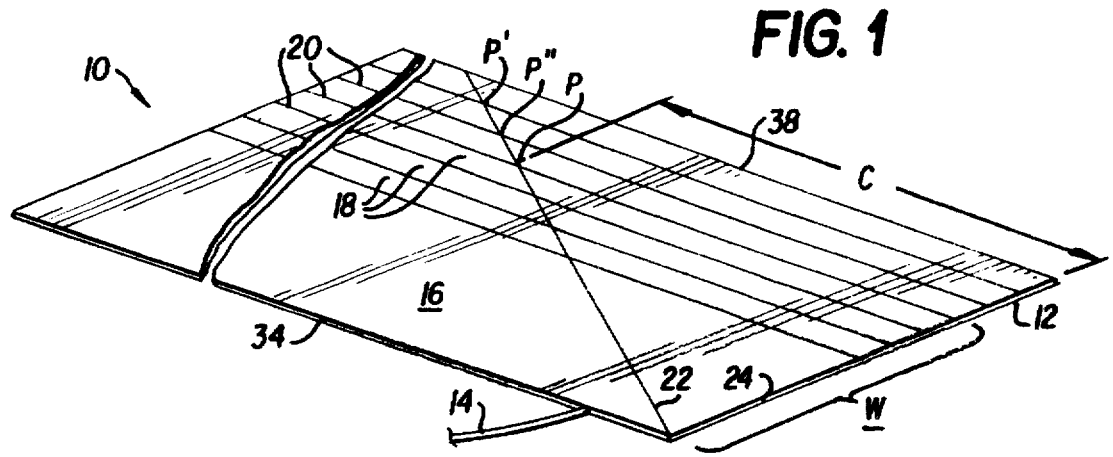
FIG. 1 is a broken perspective view of one side of a first embodiment of a blood pressure cuff in accordance with the present invention.
Figure 2:
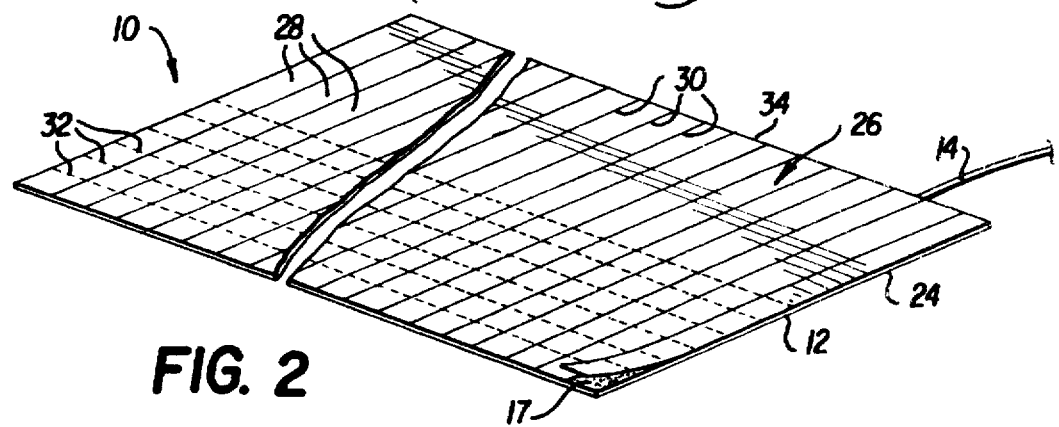
FIG. 2 is a broken perspective view of the other side of the blood pressure cuff of FIG. 1.

Referring now in detail to the drawings, there is shown in FIGS. 1 and 2 a blood pressure cuff according to the present invention which is designated by reference numeral 10. In a preferred form, the blood pressure cuff 10 has a generally rectangular shape as shown having a length sufficient to extend about a limb of the greatest circumference to be measured and to overlap itself to an extent sufficient to permit the cuff 10 to be secured permanently into an annular configuration as described hereinafter. Blood pressure cuff 10 comprises a thin-walled, inflatable bladder 12 made of rubber, synthetic elastomer or nylon which is inflated and deflated by means of a tube 14 connected to a suitable inflation/deflation device. A conventional pressure gauge (not shown) is also connected to the bladder for pressure measurement.

Referring to FIG. 1, the blood pressure cuff 10 has a first side surface 16, at least one-half of which is covered with an adhesive layer 15 (FIG. 3) protected by a plurality of peelable strips 18 extending parallel to one another along the longitudinal direction of the cuff 10. Strips 18 are preferably formed by a single sheet of material separated by cut lines 20. Perforated lines or weakened score lines may also be used. The adhesive layer 15 may be applied directly to the side surface of bladder 10, but may also be applied to a covering (not shown) for the bladder, such as, for example, a flexible fabric or other sheet material envelope bonded securely to the bladder surfaces.

As an additional feature of the invention, a generally diagonally oriented index line 22 may be applied to the first surface 16 across the surface of the bladder and peelable strips 18. This index line 22 may be a straight line having the slope x=0.4 y where x is the width dimension and y is the longitudinal dimension. Some other line, such as a curved line, may also be used based on a correlation with invasive blood pressure measurement. As described in more detail in my aforesaid patent, the optimum width W of the blood pressure cuff 10 for a patient's limb having a circumference of dimension C is determined by the intersection P of index line 22 with dimension C as measured from transverse edge 24 of the cuff 10. Point P lies on the longitudinal line along which the cuff should be folded.

Now referring to FIG. 2, the reverse or second side surface 26 of the blood pressure cuff 10 is shown. Second side surface 26 is provided over its entirety with an adhesive layer 17 protected by a plurality of peelable strips 28 extending parallel to one another along the width or transverse dimension of the cuff 10, i.e., at right angles to the strips 18. Strips 28 are, like strips 18, preferably formed from a single sheet of material separated by cut lines 30 which may be perforated lines or weakened score lines. The peelable strips 28 are also provided with perforated lines 32 extending at spaced intervals longitudinally of the cuff 10, i.e., at right angles to cut lines 28, over about one-half the surface of cuff 10. The perforated lines 32 are disposed directly opposite the peelable strips 16 on the first side surface 16 of the cuff.

The spacing between the cut lines 20 on first surface 16 may vary depending on the desired dimensional increment for folding the cuff longitudinally. The spacing between the cut lines 30 and perforated lines 32 on second surface 26 may also vary. The peelable strips 18, 28 may be made of any suitable sheet material with a release surface to be applied to the adhesive layers 15, 17. Such materials include paper or polymeric film and are well-known in the art. The adhesive layers 17, may be any suitable adhesive intended for use on or adjacent the human body in medical applications. The adhesive should form a strong bond with itself and with the material of the bladder or the bladder covering, if any.

Referring now in particular to FIGS. 3–6, the method of using the blood pressure cuff 10 of the invention will be described in greater detail. It is assumed that the proper width determination for the cuff has been made by measuring the circumference of the limb upon which the cuff is to be placed and defining the point P as described above in connection with FIG. 1.

Figure 3:
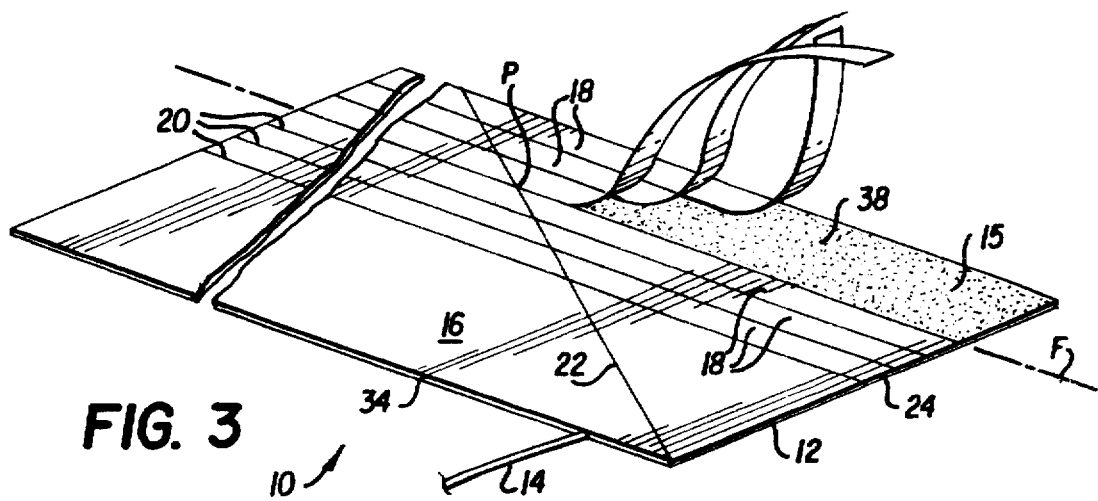
FIG. 3 is a broken perspective view of the one side of the blood pressure cuff of the invention showing a portion of the adhesive layer exposed by removal of peelable strips.

Referring to FIG. 3, since point P falls along cut line 20 at the midpoint of the six strips 18, all six of the strips 18 would be peeled away from the adhesive layer 15. The cuff 10 would then be folded longitudinally along line F which intersects point P (FIG. 3) in the direction shown by arrow A in FIG. 4 to the folded-over position shown in FIGS. 4 and 5. In this folded-over position, the cuff 10 has a width W between edge 34 and folded edge 36 which is the optimum width for the patient with limb circumference C. The folding over of the cuff 10 exposes on the first surface 16 portions of the strips 28 applied to surface 26 together with portions of the cut lines 30 and perforated lines 32.

It will be appreciated by those skilled in the art that if the circumference of the limb to be measured is greater than dimension C, fewer than all the strips 18 will have to be removed from the adhesive layer 15 on first surface 16. For example, if the circumference dimension measured from edge 24 of the cuff intersects index line 22 at point P', only two strips 18 may be peeled away and the cuff is folded over the width of one strip 18. Similarly, if the circumference dimension intersects with index 22 at point P", four strips 18 may be peeled away. For any cuff width W or less, all strips 18 may be peeled away. It is also within the scope of the invention to remove fewer strips 18 such that the adhesive layer 15 is adhered to the exposed surface of some of the remaining strips 18.

Figure 5:
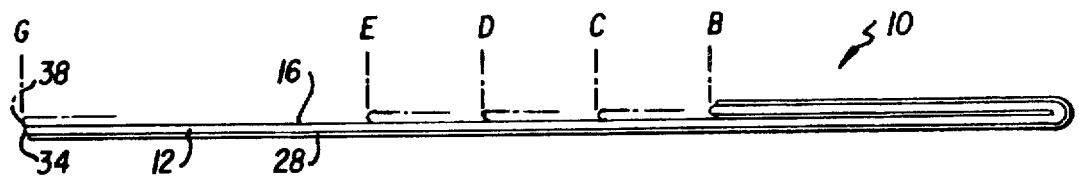
FIG. 5 is an end view of the folded-over blood pressure cuff of FIG. 4.

Preferably, the smallest folded over cuff width for the cuff 10 will be one-half the full cuff width. FIG. 5 illustrates that the cuff may be folded over to any of a number of positions, e.g., positions B, C, D, E and G, the latter position G representing the positions of the bladder edges 34, 38 (FIG. 3) when the cuff is folded in half. If desired, the entire first surface 16 of cuff 10 may be provided with an adhesive layer 15 covered by additional peelable strips 18 so that when the cuff is folded in half, for example, the adhesive layer 15 may be adhered to itself over the entire folded surface 16.

Figure 4:
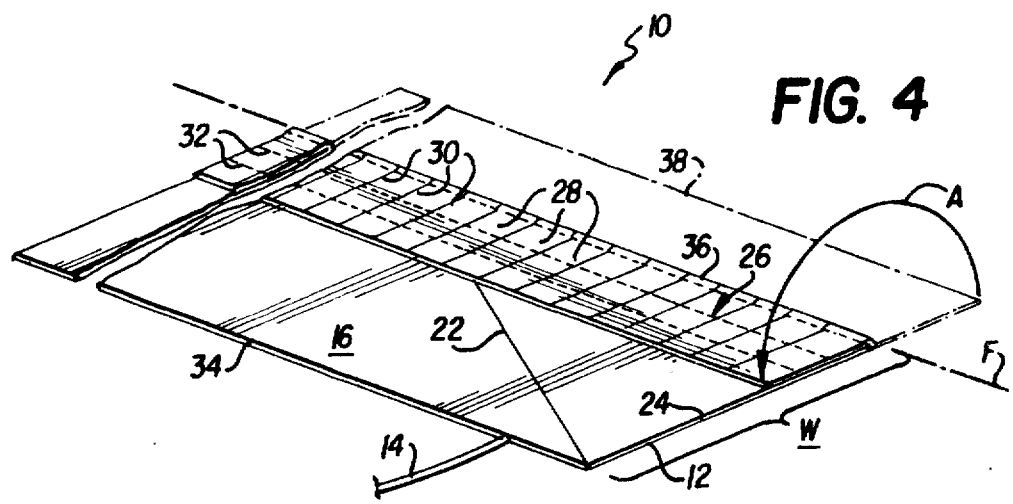
FIG. 4 is a broken perspective view of the first embodiment of the blood pressure cuff of the invention in a folded-over condition.
Figure 6:
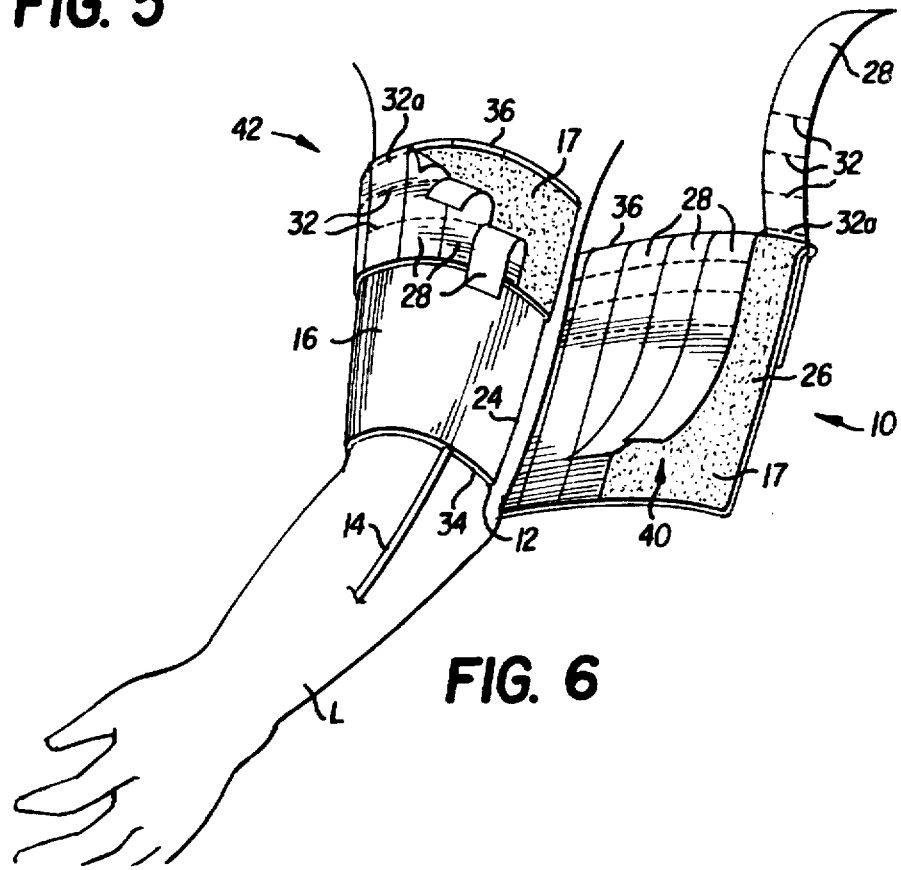
FIG. 6 is a perspective view illustrating the manner in which the folded-over blood pressure cuff is secured about the limb of a patient.

After folding to the desired width W as shown in FIG. 4, the cuff 10 is wrapped about the limb L of a patient as shown in FIG. 6 and appropriate ones of the strips 28 or portions thereof are peeled away from the adhesive layer 17 on second side surface 26 on both the inwardly facing portion 40 of second side surface 26 as well as the outwardly facing folded over portion 42 of second side surface 26.

As shown in FIG. 6, the strips 28 on the inwardly facing portion 40 are peeled away up to the perforated line 32a adjacent the folded edge 36 where the strips 28 are separated. Similarly, if desired, the strips 28 on the folded over portion 42 may be peeled away up to the perforated line 32a where they also are separated. By peeling away appropriate portions of the strips 28 on both portions 40, 42 the cuff 10 may be adhered to itself in an annular configuration with the material of the unpeeled strips 28 confronting and bearing against the patient's limb L. Alternatively, the strips 28 on the folded over portion 42 may be left in place and the adhesive layer 17 on the portion 40 may be applied to the surface of the strips 28 on the portion 42. Either way, the cuff 10 is adhesively and permanently secured into an annular or tubular configuration of the proper width for accurate blood pressure measurements. The cuff 10 may then be removed from the limb L by sliding the same downwardly as viewed in FIG. 6 over the hand of the patient and disposed of or stored for reuse on the same patient for as long as necessary, e.g., during a hospital stay of several days or weeks.

It may be desirable, especially if the cuff is to be used several times with a patient, to slide a sleeve, such as a soft fabric sleeve, over the limb L of the patient up to the location where the cuff is to be placed. Alternatively, the peelable strips may be backed with a soft material, such as felt or the like. Such a sleeve will protect the skin of the patient from chafing or discomfort that may result from contacting the skin with the peelable strips 28. After the cuff is secured about the patient's limb L, a pressure gauge and inflation device may be removably attached to the tube 14 so that the patient's blood pressure may be measured in a conventional manner.

Referring now to the second embodiment of the invention shown in FIGS. 7–10, those parts in common with the first embodiment are identified with the same reference numerals. The second embodiment of the blood pressure cuff is identified generally reference numeral 50. Cuff 50 comprises a bladder 12 which is inflated and deflated by means of a tube 14. The first side surface 16 of cuff 50 may be constructed identically with first side surface 16 of the first embodiment as shown in FIGS. 1 and 3 with peelable strips 18 separated by cut lines 20 overlying an adhesive layer 15 (not shown in FIG. 7). The second side surface 52 of cuff 50 is preferably free of any adhesive and may comprise the rubber, synthetic elastomer or nylon surface of the bladder 12.

Figure 7:
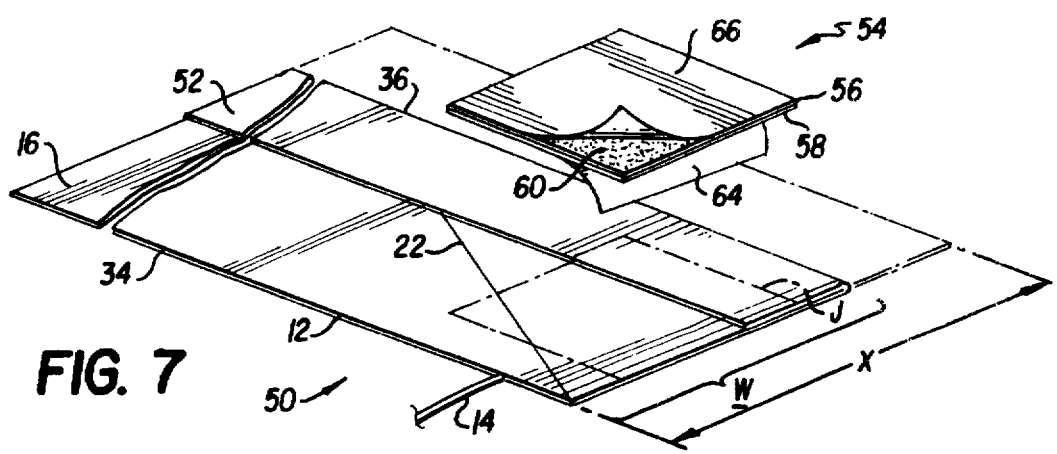
FIG. 7 is an exploded perspective view of a second embodiment of the blood pressure cuff of the invention shown in the folded-over condition.

In FIG. 7, the cuff 50 is illustrated in the folded-over condition in which it has been adjusted for the proper width W as described above in connection with FIG. 4. A polygonal (rectangular or square) fastener piece 54 of hook-and-loop fastener material, such as Velcro®, or the hook-and-loop fastener materials described in U.S. Pat. Nos. 3,387,345 or 4,672,722, is affixed to cuff 50 in the area J shown by dash-dot lines in the manner described hereinafter.

Figure 8:
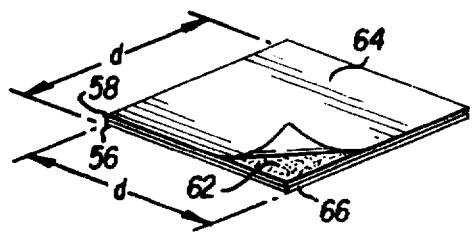
FIG. 8 is a perspective view of a hook-and-loop fastener piece used with the second embodiment of the invention.
Figure 9:
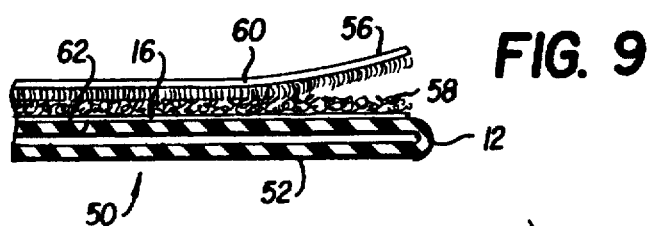
FIG. 9 is a fragmentary cross-sectional detail of the second embodiment of the blood pressure cuff of the invention.

Referring to FIGS. 7–9, fastener piece 54 comprises a square hook portion 56 and a square loop portion 58 each of which has an adhesive layer 60, 62, respectively, applied to the entire outer surface thereof. A peelable sheet 64 having the same area as portion 58 covers and protects adhesive layer 62 and a peelable sheet 66 covers and protects adhesive layer 60. Fastener piece 54 is supplied separately from cuff 50 and preferably has side dimensions d equal to approximately one-half the total width x of cuff 50 (FIGS. 7 and 8).

Figure 10:
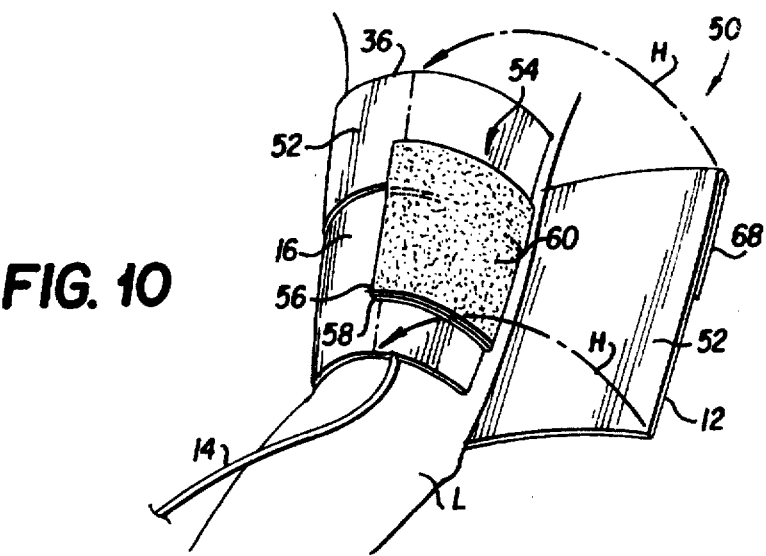
FIG. 10 is a perspective view of the folded over blood pressure cuff of the second embodiment of the invention showing the manner in which it is secured about the limb of a patient.

To use cuff 50, determining the proper folded width and folding the cuff to the position shown in FIG. 7 is carried out in the same manner as described above in connection with FIGS. 1, 3 and 4. After folding cuff 50, peelable sheet 64 is removed from adhesive layer 62 of fastener piece 54 which is then pressed against cuff 50 in area J so that adhesive layer 62 adheres to the portion of first side surface 16 and second side surface 52 enclosed by area J and the peelable strips 66 are oriented as shown in FIG. 7. Thereafter, cuff 50 is wrapped about the limb L of a patient as shown in FIG. 10 and peelable sheet 66 is removed from adhesive layer 60 so that when the cuff 50 is wrapped around limb L and brought into contact with adhesive layer 60 as shown by arrows H, the cuff 50 is secured in an annular configuration about limb L. If it is desired to remove the cuff 50 from limb L, the hook portion 56 may be separated from the loop portion 58 or, in appropriate circumstances, the cuff may simply be slid downwardly off the limb L. The second embodiment of the invention, however, provides the advantage of a circumferentially adjustable cuff, as well as a separable annular cuff configuration which is particularly useful when, for example, the patient has invasive tubes attached to the lower portion of limb L.

The quantity of the relatively expensive hook-and-loop fastener material is kept to a minimum in the second embodiment so as to maintain fabrication costs as low as possible. It is also within the scope of the invention to provide fastener pieces 54 of various dimensions and shapes including elongated strips that extend the full width W of the folded cuff 50. Preferably, the fastener pieces 54 are supplied in the form shown in FIG. 8, i.e., with the hooks fastened to the loops and the peelable sheets 64, 66 in place protecting the respective adhesive layers 62, 60.

It should be apparent that the present invention provides a low cost, adjustable and disposable blood pressure cuff adapted to be easily adjusted to the proper width for accurate blood pressure measurements. The cuff may be used for only one blood pressure measurement or for several blood pressure measurements of the same patient prior to being discarded.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A blood pressure cuff having a length and a width and a longitudinal axis along the length thereof comprising an inflatable bladder having first and second sides, said first and second sides each having an adhesive layer extending over a portion thereof, first and second peelable sheets overlying a respective adhesive layer on each side of said bladder, selected portions of each peelable sheet being adapted to be removed from each adhesive layer to expose portions thereof, said cuff being foldable along an axis substantially parallel to said longitudinal axis for adjusting said width and adhesively secured in a folded condition by the adhesive layer on said first side and wrapped about a limb of a patient and adhesively secured in an annular configuration by the adhesive layer on the second side.

2. The blood pressure cuff of claim 1, wherein said first peelable sheet comprises a plurality of first peelable strips arranged parallel to said longitudinal axis.

3. The blood pressure cuff of claim 1, wherein said second peelable sheet comprises a plurality of second peelable strips arranged substantially at right angles to said longitudinal axis.

4. The blood pressure cuff of claim 1, wherein said first peelable sheet comprises a plurality of first peelable strips having lengths arranged parallel to said longitudinal axis and said second peelable sheet comprises a plurality of second peelable strips having lengths arranged substantially at right angles to said longitudinal axis.

5. The blood pressure cuff of claim 4, wherein said first and second peelable strips are separated by cuts or perforations.

6. The blood pressure cuff of claim 5, including a plurality of perforations extending perpendicular to the lengths of said second peelable strips.

7. The blood pressure cuff of claim 4, wherein said adhesive layer on the first side is applied to substantially one-half the surface area of the first side from a longitudinal edge of the cuff to the midpoint of the width of the cuff.

8. The blood pressure cuff of claim 7, wherein said adhesive layer on the second side is applied to substantially the entire surface area of the second side.

9. The blood pressure cuff of claim 8, including a plurality of perforations extending perpendicular to the lengths of said second peelable strips.

10. The blood pressure cuff of claim 9, wherein said perforations are disposed on the second side directly opposite the adhesive layer applied to the first side.

11. The blood pressure cuff of claim 4, wherein said peelable strips are made of a paper or polymeric sheet.

12. The blood pressure cuff of claim 1, including a tube connected to said bladder for inflating the bladder.

13. The blood pressure cuff of claim 4, wherein said adhesive layer on the first side is applied to substantially the entire surface area of the first side.

14. A method of measuring blood pressure using a foldable blood pressure cuff comprising the steps of:

providing an inflatable bladder having a length and a width and a longitudinal axis along the length thereof, said bladder having first and second sides with adhesive layers extending over a portion of each side and first and second peelable strips overlying said adhesive layers on said first and second sides respectively;

peeling away selected ones of said first peelable strips to expose the adhesive layer thereunder;

adjusting the width of said cuff by folding said cuff along an axis parallel to said longitudinal axis such that a portion of the adhesive layer on the first side contacts and adheres to another portion of the adhesive layer on the first side;

wrapping the folded cuff about a limb of a patient; inflating the cuff; and measuring the blood pressure of the patient.

15. The method of claim 14, including the steps of, after wrapping the folded cuff about the limb of a patient, peeling away selected portions of the second peelable strips to expose the underlying adhesive layer on the second side and bringing separate portions of the adhesive layer on the second side into contact with one another to adhere the same together and form an annular configuration about the limb of the patient.

16. The method of claim 14, including the steps of determining the appropriate width of the cuff based on the circumference of the limb of the patient and performing said folding step such that the folded width of the cuff is substantially equal to the determined appropriate width.

17. The method of claim 16, including the step of providing an index line on said first side for determining the appropriate width of the cuff.

18. A blood pressure cuff having a length and a width and a longitudinal axis along the length thereof comprising an inflatable bladder having first and second sides, said first side having an adhesive layer extending over a portion thereof, a first peelable sheet overlying said adhesive layer on said first side of said bladder, selected portions of said peelable sheet being adapted to be removed from said adhesive layer to expose portions thereof, said cuff being foldable along an axis substantially parallel to said longitudinal axis for adjusting said width and adhesively secured in a folded condition by the adhesive layer on said first side and wrapped about a limb of a patient, and means for securing said cuff in an annular configuration about the limb of a patient.

19. The blood pressure cuff of claim 18, wherein said first peelable sheet comprises a plurality of first peelable strips arranged parallel to said longitudinal axis.

20. The blood pressure cuff of claim 19, wherein said first peelable strips are separated by cuts or perforations.

21. The blood pressure cuff of claim 19, wherein said adhesive layer on the first side is applied to substantially one-half the surface area of the first side from a longitudinal edge of the cuff to the midpoint of the width of the cuff.

22. The blood pressure cuff of claim 18, wherein said securing means comprises a fastener piece comprising hook-and-loop fastener portions, means for affixing said fastener portions between confronting portions of said cuff.

23. The blood pressure cuff of claim 22, wherein said fastener piece has opposite sides, said affixing means comprising adhesive layers applied to said opposite sides of the fastener piece for adhering said opposite sides to said confronting portions.

24. The blood pressure cuff of claim 23, wherein said fastener piece includes peelable sheets covering said adhesive layers, said sheets being peelable from said layers to expose said layers.

25. The blood pressure cuff of claim 22, wherein said fastener piece has a rectangular shape.

26. A method of measuring blood pressure using a foldable blood pressure cuff comprising the steps of:
providing an inflatable bladder having a length and a width and a longitudinal axis along the length thereof, said bladder having first and second sides with an adhesive layer extending over a portion of said first side and peelable strips overlying said adhesive layer on said first side;
peeling away selected ones of said peelable strips to expose the adhesive layer thereunder;
adjusting the width of said cuff by folding said cuff along an axis parallel to said longitudinal axis such that a portion of the adhesive layer on the first side contacts and adheres to another portion of the adhesive layer on the first side;
wrapping the folded cuff about a limb of a patient;
inflating the cuff; and
measuring the blood pressure of the patient.

27. The method of claim 26, including the steps of, after wrapping the folded cuff about the limb of a patient, applying a fastener piece between confronting portions of said cuff and adhesively affixing said fastener piece between said confronting portions to adhere the same together and form an annular configuration about the limb of the patient.

28. The method of claim 26, including the steps of determining the appropriate width of the cuff based on the circumference of the limb of the patient and performing said folding step such that the folded width of the cuff is substantially equal to the determined appropriate width.

29. The method of claim 27, wherein said fastener piece comprises a hook-and-loop fastener piece and including the step of, after forming the cuff into an annular configuration about the limb of the patient, separating the hook-and-loop fastener piece and removing the cuff from the limb of the patient.

* * * * *